United States Patent
Kwok et al.

(10) Patent No.: US 9,964,540 B2
(45) Date of Patent: May 8, 2018

(54) DETECTION OF AN IMMUNE RESPONSE

(71) Applicant: Benaroya Research Institute, Seattle, WA (US)

(72) Inventors: William W. Kwok, Bellevue, WA (US); Erik Wambre, Seattle, WA (US)

(73) Assignee: Benaroya Research Institute, Seattle, WA (US)

( * ) Notice: Subject to any disclaimer, the term of this patent is extended or adjusted under 35 U.S.C. 154(b) by 0 days. days.

(21) Appl. No.: 15/652,560

(22) Filed: Jul. 18, 2017

(65) Prior Publication Data

US 2017/0315123 A1 Nov. 2, 2017

Related U.S. Application Data

(60) Division of application No. 14/990,126, filed on Jan. 7, 2016, now Pat. No. 9,733,247, which is a continuation of application No. 13/974,575, filed on Aug. 23, 2013, which is a continuation of application No. PCT/US2012/026592, filed on Feb. 24, 2012, now abandoned.

(60) Provisional application No. 61/446,797, filed on Feb. 25, 2011.

(51) Int. Cl.
  *G01N 33/00* (2006.01)
  *A61K 39/35* (2006.01)
  *A61K 39/36* (2006.01)
  *G01N 33/569* (2006.01)
  *G01N 33/68* (2006.01)

(52) U.S. Cl.
  CPC ....... *G01N 33/56977* (2013.01); *A61K 39/35* (2013.01); *G01N 33/56972* (2013.01); *G01N 33/6893* (2013.01); *G01N 2333/70514* (2013.01); *G01N 2333/70596* (2013.01); *G01N 2333/726* (2013.01); *G01N 2800/24* (2013.01)

(58) Field of Classification Search
  None
  See application file for complete search history.

(56) References Cited

U.S. PATENT DOCUMENTS

| | | | |
|---|---|---|---|
| 5,508,167 | A | 4/1996 | Roses et al. |
| 5,843,780 | A | 12/1998 | Thomson |
| 6,027,896 | A | 2/2000 | Roses et al. |
| 6,933,148 | B2 | 8/2005 | Collins et al. |
| 7,094,555 | B2 | 8/2006 | Kwok et al. |
| 7,713,688 | B2 | 5/2010 | Collins |
| 2002/0052490 | A1 | 5/2002 | Ball et al. |
| 2003/0202980 | A1 | 10/2003 | Caplan et al. |
| 2005/0260662 | A1 | 11/2005 | Yang |
| 2006/0024334 | A1 | 2/2006 | Larche et al. |
| 2008/0279813 | A1 | 11/2008 | Hall et al. |
| 2009/0214580 | A1 | 8/2009 | Houghten et al. |
| 2009/0226471 | A1 | 9/2009 | Kwok et al. |

FOREIGN PATENT DOCUMENTS

| | | |
|---|---|---|
| RU | 2302635 C1 | 7/2007 |
| WO | WO 2009/124954 A1 | 10/2009 |
| WO | WO 2012/148549 A1 | 11/2012 |

OTHER PUBLICATIONS

Buchanan et al. 'Egg oral immunotherapy in nonanaphylactic children with egg allergy.' J. Allergy Clin. Immunol. 119:199-205, 2007.*
Wambre et al. 'A phenotypically and functionally distinct human TH2 cell subpopulation is associated with allergic disorders.' Sci Transl. Med. 9, eaam9171 (2017).*
Hofmann et al. 'Safety of a peanut oral immunotherapy protocol in children with peanut allergy.' J. Allergy Clin. Immunol. 124:286-291, 2009.*
Delong JH et al. Ara h 1-reactive T cells in peanut allergic individuals. J. Allergy Clin Immunol. May 2011; 127(5): 1211-8.e3. doi:10.1016/j.jaci.2011.02.028.
Supplementary European Search Report, EP 12777751, dated Oct. 15, 2014.
Kwok WW et al. Direct ex vivo analysis of allergen-specific CD4+ T cells. Journal of Allergy and Clinical Immunology. Jun. 1, 2010; 125(6): 1407-1409.e1.
Kinnunen T et al. Allergen-specific naïve and memory CD4+ T cells exhibit functional and phenotypic differences between individuals with our without allergy. European Journal of Immunology. Jul. 13, 2010; 40(9): 2460-2469.
Cosmi L et al. Identification of a novel subset of human circulating memory CD4+ T cells that produce both IL-17A and IL-4. Journal of Allergy and Clinical Immunology. Jan. 1, 2010; 125(1): 222-230.
Maggi L et al. CD161 is a marker of all human IL-17-producing T-cell subsets and is induced for RORC. European Journal of Immunology. Aug. 1, 2010; 40(8): 2174-2181.
Cosmi L et al. Human interleukin 17-producing cells originate from a CD161+CD4+ T cell precursor. Journal of Experimental Medicine. Jan. 1, 2008; 205(8): 1903-1916.
Van Overtvelt L et al. Assessment of Bet v 1-specific CD4+ T cell responses in allergic and nonallergic individuals using MHC class II peptide tetramers. Journal of Immunology. Mar. 19, 2008; 180(7): 4514-4522.
International Search Report and Written Opinion, PCT/US2011/026244, dated Aug. 1, 2011.
Francis et al., Peptide-based vaccination: where do we stand? Current Opinion in Allergy and Clinical Immunology 2005, 5:537-543.
Oppenheimer et al., Treatment of peanut allergy with rush immunotherapy. J Allergy Clin Immunol 1992; 90(2):256-62 Abstract only.

(Continued)

*Primary Examiner* — Nora Rooney
(74) *Attorney, Agent, or Firm* — Myers Bigel, P.A.

(57) ABSTRACT

Provided herein are methods of detecting and/or monitoring the presence or severity of an immune disorder in a subject, including detecting a frequency of a Th2a subset of CD4+ T cells in a biological sample of the subject. In some embodiments, the detecting includes: (a) detecting a frequency of CD4+ T cells in a biological sample of said subject; (b) detecting a frequency of a Th2a subset of the CD4+ T cells in the biological sample; and (c) comparing the frequency of the Th2a subset with the frequency of the CD4+ T cells.

17 Claims, 3 Drawing Sheets

(56) References Cited

OTHER PUBLICATIONS

Nelson et al., Treatment of anaphylactic sensitivity to peanuts by immunotherapy with injections of aqueous peanut extract. J Allergy Clin Immunol 1997; 99(6 Pt 1):744-51 Abstract only.
Bock et al., Further fatalities caused by anaphylactic reactions to food, 2001-2006. J Allergy Clin Immunol 2007; 119(4):1016-8 Abstract only.
Hofmann et al., Safety of a peanut oral immunotherapy protocol in children with peanut allergy. J Allergy 354 Clin Immunol 2009; 124(2):286-91, 291. 355.
Jones et al., Clinical efficacy and immune regulation with peanut oral immunotherapy. J Allergy Clin Immunol 2009; 357 124(2):292-300, 300.
Blumchen et al., Oral peanut immunotherapy in children with peanut anaphylaxis. J Allergy Clin Immunol 360 2010; 126(1):83-91.
Kwok WW et al., Rapid epitope identification from complex class-II-restricted T-cell antigens. Trends in Immunology. Nov. 2001; 22(11): 583-588.
Hakonarson H et al. Autologously up-regulated Fc receptor expression and action in airway smooth muscle mediates its altered responsiveness in the atopic asthmatic sensitized state. PNAS. Apr. 1998; 95: 5257-5262.
DeGroot AS et al. Activation of natural regulatory T cells by IgG Fc-derived peptide "Tregitopes". Blood. Oct. 15, 2008; 112(8): 3303-3311.
Macaubas C et al. Allergen-specific MHC Class II tretramer + cells are detectable in allergic, but not in nonallergic, individuals. The Journal of Immunology. 2006; 176: 5069-5077.
He X-S et al. Direct functional analysis of epitope-specific CD8+ T cells in peripheral blood. Viral Immunology. 2001; 14(1): 59-69.
Wurtzen PA et al. Identification of isoform-specific T-cell epitopes in the major timothy grass pollen allergen, Phl p. 5. Clinical and Experimental Allergy. 1999; 29: 1614-1625.

Schenk S et al. T-cell epitopes of Phl p. 1, major pollen allergen of timothy grass (*Phleum pratense*): evidence for crossreacting and non-crossreacting T-cell epitopes within grass group I allergens. J Allergy Clin Immunol. Dec. 1995; 96(6) part 1: 986-996.
Wang Y-H et al. A novel subset of CD4+ Th2 memory/effector cells that produce inflammatory IL-17 cytokine and promote the exacerbation of chronic allergic asthma. J Exp Med. Oct. 25, 2010; 207(11): 2479-2491.
Novikov PD et al. The principles of evaluation of immune status and diagnostic of immunodeficiency diseases. Immunopathology, Allergology, Infectology. 2005; 2: 8-22. English summary.
Conti F and Orlandini A. Treatment of allergic manifestations with transfer factor (TF). Physiologic Regulating Medicine. 2006; 1: 31-34.
Adkis M et al. Immune responses in healthy and allergic individuals are characterized by a fine balance between allergen-specific T regulatory 1 and T helper 2 cells. J Exp Med. Jun. 7, 2004; 199(11): 1567-1575.
Dong C and Martinez GJ. T cells: the usual subsets. Nature Reviews Immunology. 2010. Poster (online). 1 page. Retrieved Apr. 16, 2012.
Cosmi L et al. CRTH2 is the most reliable marker for the detection of circulating human type 2 Th and type 2 T cytotoxic cells in health and disease. Eur J Immunol. 2000; 30: 2972-2979.
International Search Report and Written Opinion, PCT/US2012/026592, dated Jun. 7, 2012.
Wambre E et al. Th2A cells as a unique Th2 cell subset in allergic individuals: steps toward a T cell biomarker for allergy. J Allergy Clin Immunol. Abstracts. AB129(2): 490, 2012.
European Patent Office Examination Report, EP 12777751.4, dated Jan. 27, 2017.
Iwasaki M et al. Association of a new-type prostaglandin D2 receptor CRTH2 with circulating T helper 2 cells in patients with atopic dermatitis. The Journal of Investigative Dermatology. 2002; 119: 609-616.
European Patent Office Examination Report, EP 12777751.4, dated Nov. 16, 2017, 9 pages.

* cited by examiner

DETECTION OF AN IMMUNE RESPONSE

RELATED APPLICATIONS

This application is a divisional of U.S. patent application Ser. No. 14/990,126, filed Jan. 7, 2016, now allowed, which is a continuation of U.S. patent application Ser. No. 13/974,575, filed Aug. 23, 2013, which is a continuation under 35 U.S.C. 111(a) of PCT Application No. PCT/US2012/026592, filed Feb. 24, 2012, which in turn claims the benefit of U.S. Provisional Patent Application Ser. No. 61/446,797, filed Feb. 25, 2011, the disclosure of each of which is incorporated by reference herein in its entirety.

STATEMENT OF GOVERNMENT SUPPORT

This invention was made with Government support under contract number HHSN272200700046C awarded by the National Institutes of Health. The Government has certain rights in the invention.

FIELD OF THE INVENTION

The present invention is in the field of immunology and immunology-based testing and/or monitoring.

BACKGROUND

Allergen specific immunotherapy (SIT) is the only treatment available that treats the cause of an allergy. However, the therapy typically lasts from 3 to 5 years, with a widely-ranging efficacy rate of 50-90%. The ability to monitor the progress of SIT would allow better predictions of efficacy as well as the more precise tailoring to the patient populations being treated with this long and expensive therapy.

In addition, the ability to accurately detect and/or monitor an immune response could aid in the diagnosis and treatment of immune-related disorders, including allergy and infection.

SUMMARY

Provided herein are methods of detecting an immune disorder in a subject, including detecting (e.g., in vitro) a frequency of an allergen-specific Th2 subset (Th2a) of CD4+ T cells in a biological sample of (or collected from) the subject (e.g., a whole blood sample or a peripheral blood mononuclear cell (PBMC) sample). In some embodiments, the detecting includes: (a) detecting a frequency of CD4+ T cells in a biological sample of (or collected from) said subject; (b) detecting a frequency of a Th2a subset of the CD4+ T cells in the biological sample; and (c) comparing the frequency of the Th2a subset with the frequency of the CD4+ T cells. In some embodiments, a higher frequency of Th2a cells as compared to a control subject indicates an immune disorder.

In some embodiments, the CD4+ T cells are total CD4+ T cells. In some embodiments, the CD4+ T cells are total memory CD4+ T cells. In some embodiments, the CD4+ T cells are total CRTH2+ CD4+ T cells.

In some embodiments, a frequency of at least 50, at least 60, or at least 70 Th2a cells per 100,000 total CD4+ cells (or at least 500, at least 600, or at least 700 Th2a cells per one million CD4+ cells) indicates that said subject has an immune disorder. In some embodiments, a frequency of at least 60, 65, 75, 80, 85, 90, 95 or 100 Th2a cells per 100,000 total memory CD4+ T cells. In some embodiments, a frequency of at least 1,000, 2,000, 3,000, 4,000 or 5,000 Th2a cells per 100,000 total CRTH2+ CD4+ T cells indicates that said subject has an immune disorder.

In some embodiments, the immune disorder is an allergic disorder, e.g., seasonal rhinoconjuctivitis, animal dander allergy, food allergy, or venom anaphylaxis.

In some embodiments, the CD4+ Th2a cells are CD161 positive, CRTH2 positive, CD27 negative, CD49d positive and/or CD45RB negative.

Also provided are methods of monitoring immune deviation in a subject (e.g., during a course of an immunotherapy treatment), including detecting a frequency of a Th2a subset of CD4+ T cells in a biological sample of the subject (e.g., a whole blood sample or a peripheral blood mononuclear cell (PBMC) sample). In some embodiments, the monitoring includes: (a) detecting a first frequency of CD4+ Th2a cells as compared to a frequency of total CD4+ cells in a first biological sample of said subject; and then (b) detecting a second frequency of CD4+ Th2a cells as compared to a frequency of total CD4+ cells in a second biological sample of said subject, wherein a lower number for the second frequency of said CD4+ Th2a in step (b) as compared to the first frequency in step (a) indicates immune deviation in said subject.

In some embodiments, the second biological sample is collected from about 2, 4, or 6 weeks to about 1, 2, 3, 4 or 5 years after the first biological sample is collected from the subject.

In some embodiments, the CD4+ Th2a cells are CD161 positive. In some embodiments, the CD4+ Th2a cells are CD161 positive, CRTH2 positive, CD27 negative, CD49d positive and/or CD45RB negative.

In some embodiments, the detecting step is carried out by fluorescent activated cell sorting (FACS) (e.g., with a 4-, 5-, 6-, or 7-color combination).

Also provided is the use of a CD4+ Th2a cell frequency for detecting an immune disorder in a subject (e.g., an allergy), or for monitoring an immune deviation in a subject.

Methods of treating an immune disorder in a subject are further provided, comprising: detecting a Th2a cell frequency in said subject; and then, if the Th2a cell frequency is significant, administering an immunotherapy treatment to said subject.

In some embodiments, the immunotherapy treatment is oral immunotherapy treatment (OIT), sublingual immunotherapy (SLIT), or subcutaneous immunotherapy (SCIT) treatment.

In some embodiments, a significant Th2a cell frequency is greater than about one cell per 500, 1,000, or 5,000 total CD4+ T cells or per total CD45RO+ (memory) T cells. In some embodiments, a significant Th2a cell frequency is greater than about one cell per 10, 20, 30, 40, 50, 60, 70, 80, 90 or 100 total CRTH2+ CD4+ T cells.

Further provided is the use of a means for detecting CD4+ Th2a T cell frequency in a biological sample (e.g., immunoassay, flow cytometry, FACS, etc.) for carrying out a method as taught herein.

DETAILED DESCRIPTION OF THE PREFERRED EMBODIMENTS

Figure 1:
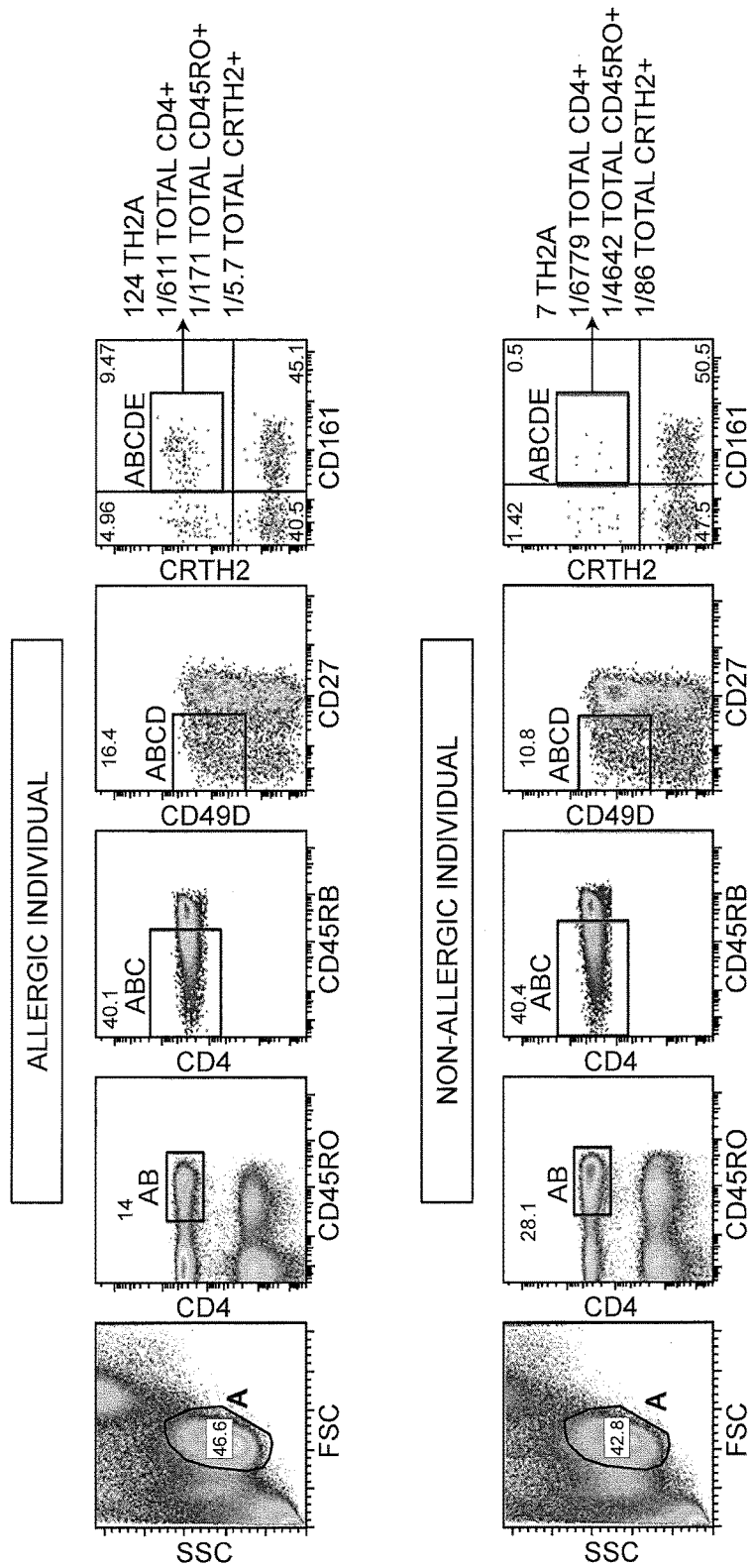
FIG. 1 presents a FACS plot showing that allergen-specific Th2 cells (Th2a) are a subset of Th2 cells expressing CD161 and CD49d, and lacking CD27 and CD45RB expression.

Provided herein are methods for the determination of an immune response, including, but not limited to, an allergy response based upon detection of allergy-specific CD4+ T cell phenotype and/or the frequency of said phenotype in a patient or patient sample. This determination is useful for, inter alia, detecting or monitoring an allergy and/or the effectiveness of immunotherapy.

The disclosures of all United States patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

An "immune response" elicited, detected and/or monitored can be a protective immune response, a cellular immune response, a humoral immune response, a Th1 immune response, a Th2 immune response, or any combination thereof. Detection and/or monitoring of the immune response may be useful, e.g., in monitoring immune function and/or response to an antigen, e.g., for autoimmune disease, a pathogen, cancer, diabetes or multiple sclerosis, or to test the effectiveness of a vaccine or vaccination.

An "immune disorder" is a disease or illness associated with an immune response, including, but not limited to, allergy or allergic disorder, autoimmune disease, pathogen infection, cancer, diabetes, multiple sclerosis, etc.

An "allergy", "allergic disorder", or "allergic disease" is a disorder in which the immune system is hypersensitive to normally harmless environmental substances. These environmental substances that cause allergies are called "allergens." Common allergic diseases include seasonal rhinoconjuctivitis (e.g., allergies to grasses and pollen such as ragweed, timothy grass), allergies to pet dander such as cat dander or dog dander, food allergies such as peanut, dairy and wheat allergies, venum anaphylaxis, and asthma. Production of the "IgE" form of antibody is associated with allergic reaction. The IgE antibody causes excessive activation of mast cells and basophils, resulting in an overreactive inflammatory response, which can be severe enough to result in anaphylactic shock. Thus, in some embodiments the IgE antibody may also be measured, if desired.

An "antigen" as used herein is a molecule or molecule fragment that is able to bind specifically to a major histocompatibility complex (MHC) molecule for presentation to the immune system cells, which complex of molecule or molecule fragment and MHC molecule, in turns, binds to immune system cell receptors (e.g., T cell receptors). An "immunogen" is a particular type of antigen that is able to provoke a humoral and/or cell mediated immune response if injected on its own. Antigens are usually proteins or polysaccharides, including parts (coats, capsules, cell walls, flagella, fimbrae, and toxins) of bacteria, viruses, and other microorganisms. Lipids and nucleic acids are normally only antigenic when combined with proteins and polysaccharides. Non-microbial exogenous (non-self) antigens can include pollen, egg white or other food antigens, and proteins from transplanted tissues and organs or on the surface of transfused blood cells. A "vaccine" is an example of immunogenic antigens intentionally administered to induce acquired immunity in the recipient.

Though not wishing to be bound by theory, it is thought that an allergic reaction begins when an MHC class II molecule of an antigen-presenting cell binds to and presents an allergen or portion thereof to CD4+ T cells of the immune system, which, in turn, elicit an immune response to that allergen. An "immune response" elicited, detected and/or monitored can be a protective immune response, a cellular immune response, a humoral immune response, a Th1 immune response, a Th2 immune response, or any combination thereof. Detection and/or monitoring of the immune response may be useful, e.g., in monitoring immune function and/or response to an antigen, e.g., for autoimmune disease, cancer, diabetes or multiple sclerosis, or to test the effectiveness of a vaccine or vaccination.

As noted above, common allergens include, but are not limited to, pollens, animal dander (e.g., cat or dog dander), grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens also include those from molds or fungi such as *Alternaria, Fusarium, Hormodendrum, Aspergillus, Micropolyspora, Mucor*, and thermophilic *Actinomyces*; epidermal allergens can be obtained from house or organic dusts (typically fungal in origin), from arthropods such as house mites (*Dermatophagoides pteronyssinus*), or from animal sources such as feathers, cat and dog dander; common food allergens include milk and cheese (diary), egg, wheat, nut (e.g., peanut), seafood (e.g., shellfish), pea, bean and gluten allergens; common environmental allergens include metals (e.g., nickel and gold), chemicals (e.g., formaldehyde, trinitrophenol and turpentine), latex, rubber, fiber (e.g., cotton or wool), burlap, hair dye, cosmetic, detergent and perfume allergens. Common drug allergens include local anesthetic and salicylate allergens; antibiotic allergens include penicillin, tetracycline and sulfonamide allergens; and common insect allergens include bee, wasp and ant venom, and cockroach calyx allergens.

Symptoms of an allergy include, but are not limited to, sneezing, runny nose and/or nasal congestion, difficulty breathing, cramps, rash, vomiting, etc. Common symptoms of a food allergy can include wheezing and difficulty breathing, itchy skin rashes, including hives, vomiting, diarrhea, nausea, abdominal pain, and swelling around the mouth and in the throat. Food allergies in children can range from mild to severe, though many will outgrow the allergies by age three. Common food allergies in children under 18 years of age include nut (e.g., peanuts), egg, fin fish, strawberry, wheat, and soy.

In some embodiments, detection of the allergic reaction as taught herein is useful for determining if particular symptoms are due to an allergy. Monitoring the allergy as taught herein is also useful to determine if the allergy is decreasing in severity (e.g., the child is outgrowing the allergy, for example, by measuring and comparing an immune deviation at about 0, 1, 2, 3, 4, 5, 6, 7, or 8 years of age).

"CD4+ T cells," also known as "helper T cells" or "Th," are a type of white blood cell and express the CD4 protein on their surface. Activated CD4+ T cells differentiate into at least the two major subtypes, "Type 1" ("Th1") and "Type 2" ("Th2"), as well as "Type 17" ("Th17") and "T regulatory" ("Treg"). In some embodiments, CRTH2 and/or lack of CD27 expression is used as a Th2 marker. The analysis of markers such as CRTH2 and/or CD27 within allergen-specific CD4+ T cells allows the determination of the allergen-specific T cells subset (Th1 or Th2). This, in turn, may be used to predict the effectiveness of allergen-specific immunotherapy in a patient during desensitization based upon the patient's HLA genotype. For example, after excluding monocytes, macrophages, dendritic cells and B cells (CD14 and CD19 positive cells), CD4+ T lymphocytes may be analyzed.

"Memory CD4+ T cells" as used herein is a subtype of CD4+ T cells that are also CD45RO positive.

"CRTH2+ T cells" as used herein is a subtype of CD4+ T cells that are also CRTH2 positive.

As taught herein, the Th2 response, and a subtype of Th2, in particular, is associated with an allergic reaction. This subtype is referred to herein as "Th2a." CD4+ T cells having a Th2a phenotype have one or more of the following marker profiles: CRTH2+, CD27−, CD161+, CD49d+, CD45RB−. The presence of a significant number of Th2a cells (i.e., frequency) is associated with an allergy or other immune disorder.

In particular embodiments, a frequency of 0, 1, 2, or 5, up to 20, 30, 40, or 49 Th2a cells per 100,000 CD4+ T cells indicates the absence of an immune disorder, such as an allergy, whereas a frequency of at least 50, at least 60, at least 70, or at least 80 Th2a cells per 100,000 CD4+ T cells indicates an immune disorder, such as an allergy. In some embodiments, a frequency of 50, 60, 70, 80, 90, or 100, up to about 300, 400, 500, 600, 700, 800, 900, or 1,000 Th2a cells per 100,000 CD4+ T cells (e.g., memory T cells, CRTH2+ T cells) indicate an immune disorder, such as an allergy.

Allergen-specific CD4+ Th2 cells ("Th2a") according to some embodiments can be identified as $CD4^{pos}$ $CRTH2^{pos}$ $CD27^{neg}$ $CD49d^{pos}$ $CD45RB^{neg}$ and $CD161^{pos}$ (i.e., having a significant number of $CD161^{pos}$ cells) whereas non-allergen-specific CD4+ Th2 cells can be identified as having $CD4^{pos}$ $CRTH2^{pos}$ $CD161^{neg}$ (i.e., having a comparatively lower frequency of $CD161^{pos}$ cells as taught herein). The overall number and/or percentage of Th2a cells in the Th2 phenotype may in some embodiments correlate with the severity of the allergy or other immune disorder in a subject. A decrease in the number and/or percentage of Th2a cells in the Th2 phenotype may indicate an immune deviation, for example, in response to immunotherapy.

Detection of one or more of these markers may be performed using techniques commonly known in the art. See, e.g., U.S. Pat. No. 7,713,688 to Collins and U.S. Pat. No. 6,933,148 to Collins et al., which are incorporated by reference herein.

CD4 is a glycoprotein expressed on the surface of T helper cells, regulatory T cells, monocytes, macrophages, and dendritic cells. T cells expressing CD4 are also known as CD4+ T cells. CD4 is a co-receptor that assists the T cell receptor (TCR) to activate its T cell following an interaction with an antigen presenting cell. Using its portion that resides inside the T cell, CD4 amplifies the signal generated by the TCR by recruiting an enzyme, known as the tyrosine kinase lck, which is essential for activating many molecules involved in the signaling cascade of an activated T cell. CD4 also interacts directly with MHC class II molecules on the surface of the antigen presenting cell using its extracellular domain.

CRTH2 (Chemoattractant receptor-homologous molecule expressed on Th2 lymphocytes) is a cognate receptor for prostaglandin (PG) $D_2$, and is suggested to play a functional rule in Th2-dependent allergic inflammation. The high expression levels of CRTH2 in Th2 lymphocytes, basophils and eosinophils imply a major role of CRTH2 in allergic diseases. CRTH2 is a reliable marker for the detection of human Th2.

CD45RO is expressed on $CD4^+$ and $CD8^+$ T memory cells as well as on $CD4^+$ effector T cells. CD45RO is also expressed on monocytes, macrophages, and granulocytes.

CD27 is a member of the TNF-receptor superfamily. This receptor is required for generation and long-term maintenance of T cell immunity. It binds to ligand CD70, and plays a key role in regulating B-cell activation and immunoglobulin synthesis. It is thought to be downregulated on terminally differentiated effector cells, which could be in that state because of repeated antigenic stimulation.

CD161 is a C-type lectin receptor (NKR-P1A). The function of CD161 is undefined, but it may play a role in T cell migration from circulation into tissue, or may act as a co-stimulatory receptor. CD161 is a marker of human IL-17-producing T cells and is induced by retinoic acid-related orphan receptor C (RORC).

CD49d, or integrin alpha 4 (VLA4), is thought to be involved in lymphocyte migration from circulation into tissue by strengthening lymphocyte adhesion to endothelial cells.

CD45RB, is an isoform of CD45 with exon 5 splicing (encodes B determinant). It is involved in TCR and BCR signaling. As T cells become activated and progress from naïve to memory cells, CD45RB expression is normally downregulated. Additionally, functionally distinct $CD4^+$ T cell subsets, which secrete differing cytokine profiles, can be separated by CD45RB intensity.

In some embodiments, markers are detected using a suitable immunological technique, e.g., flow cytometry for membrane-bound markers, immunohistochemistry for intracellular markers, and enzyme-linked immunoassay for markers secreted into the medium. The expression of protein markers can also be detected at the mRNA level by, e.g., reverse transcriptase-PCR using marker-specific primers. See, e.g., U.S. Pat. No. 5,843,780, which is incorporated by reference herein.

In some embodiments, the assay makes use of flow cytometry (e.g., FACS) for analyzing the phenotype and/or frequency of CD4+ T cells. CD4+ T cells in some embodiments are analyzed with a gating tool configured to detect and gate based upon predetermined markers and/or molecule detection.

T cells can be provided in a biological sample from a subject. Suitable samples can include, for example, blood, lymph, lymph nodes, spleen, liver, kidney, pancreas, tonsil, thymus, joints, synovia, and other tissues in which T cells may be found. T cells may be isolated, for example, as peripheral blood mononuclear cells (PBMC). PBMC can be partially purified, for example, by centrifugation (e.g., from a buffy coat), by density gradient centrifugation (e.g., through a Ficoll-Hypaque), by panning, affinity separation, cell sorting (e.g., using antibodies specific for one or more cell surface markers), and other techniques that provide enrichment of PBMC and/or T cells. See, e.g., U.S. Pat. No. 7,713,688 to Collins and U.S. Pat. No. 6,933,148 to Collins et al., which are incorporated by reference herein.

In some embodiments, and for ease of use, the biological sample provided for the testing disclosed herein is whole blood without prior purification and/or enrichment of PBMC and/or T cells. In some embodiments, only a small sample is required for testing as described herein, e.g., between 0.1, 0.5, 1 or 2, and 3, 5, 8 or 10 milliliters of a whole blood sample.

Though not required, in some embodiments MHC class II tetramer staining may also used in order to detect the CD4+ T cell phenotype and/or frequency based upon a predetermined MHC class II molecule-antigen complex. Major histocompatibility complex (MHC) class II tetramers allow the direct visualization of antigen specific CD4+ T cells by flow cytometry. See U.S. Pat. No. 7,094,555 to Kwok et al., which is incorporated by reference herein. This method relies on the highly specific interaction between the peptide-loaded MHC class II molecule and its corresponding T-cell receptor. While the affinity of a single MHC/peptide molecule is low, cross-linking MHC/peptide complexes with streptavidin increases the affinity of the interaction, enabling their use as staining reagents.

In some embodiments, detecting the CD4+ phenotype may also include detecting cytokine production. Cytokines associated with Th2 include interleukin-4, interleukin-5, interleukin-6, interleukin-10, and interleukin-13. In contrast, cytokines associated with Th1 are associated with a normal, non-allergic response to an antigen. Cytokines associated with Th1 include interferon-γ and tumor necrosis factor-alpha.

As taught herein, in some embodiments monitoring a Th2 response in a subject, and Th2a, in particular, is useful in immunotherapy. "Specific immunotherapy" or "allergen-specific immunotherapy" is the administration of gradually increasing doses of crude extracts of allergens, making subjects tolerant to them (see, e.g., Francis et al., Peptide-based vaccination: where do we stand? Curr Opin Allergy and Clin Immunology 2005, 5:537-543).

Successful allergen-specific immunotherapy is associated with "immune deviation," i.e., the switch from the allergen-specific Th2 response typical for allergic patients (e.g., $CD4^+$ $CRTH2^+$ $CD27^-$) to a more Th1/Treg response characteristic for non-allergic individuals (e.g., $CD4^+$ $CRTH2^-$ $CD27^+$). See, e.g., U.S. Patent Application Publication No. 2009/0214580 to Houghten et al.

As taught herein, allergen-specific CD4+ Th2 cells ("Th2a") according to some embodiments can be identified as $CD4^{pos}$ $CRTH2^{pos}$ $CD27^{neg}$ $CD49d^{pos}$ $CD45RB^{neg}$ $CD161^{pos}$ (i.e., having a significant number of $CD161^{pos}$ cells), whereas non-allergen-specific CD4+ Th2 cells can be identified as $CD4^{pos}$ $CRTH2^{pos}$ $CD161^{neg}$ (i.e., having a comparatively lower number of $CD161^{pos}$ cells as taught herein). The overall number and/or percentage of Th2a cells in the Th2 phenotype may in some embodiments correlate with the severity of the allergy in a subject. In some embodiments, a decrease in the number and/or percentage of Th2a cells in the Th2 phenotype may indicate an immune deviation in response to immunotherapy (e.g., $CD4^{pos}$ $CRTH2^{pos}$ $CD27^{neg}$ $CD49d^{pos}$ $CD45RB^{neg}$ $CD161^{pos}$ frequency lower than 30, 40 or 50 per 100,000 of CD4+ cells, and/or lower than 30, 40, or 50 per 100,000 of memory CD4+ T cells, and/or lower than 500, 1,000, or 2,000 per 100,000 of CRTH2+ T cells).

In some embodiments, a significant Th2a cell frequency indicating an immune disorder is greater than about one cell per 500, 1,000, or 5,000 total CD4+ T cells or per total CD45RO+ (memory) T cells. In some embodiments, a significant Th2a cell frequency is greater than about one cell per 10, 20, 30, 40, 50, 60, 70, 80, 90 or 100 total CRTH2+ CD4+ T cells.

In some embodiments, immune deviation is measured by an increase in the ratio of Th1/Th2 response, e.g., by 1, 5, or 10, to 20, 15 or 100-fold. In some embodiments, immune deviation is measured by the change in the ratio of Th2a/CD4 T cell response, and/or Th2A/memory CD4+ T cell response, and/or Th2A/CRTH2+ T cell response, and/or Th2a/Th1 response, e.g., by 1, 5, or 10, to 20, 15 or 100-fold.

In some embodiments, immune deviation may also be measured by the change in the ratio of IgG to IgE antibodies specific for the allergen being administered. In some embodiments, immune deviation is measured by an increase in the IgG/IgE ratio, e.g., in which this ratio increases by 1, 5, or 10, to 20, 15 or 100-fold.

Immune deviation may be monitored in a subject undergoing immunotherapy by detecting the phenotype and/or frequency of Th2 and/or Th2a cells in the subject, and then again after one or more administrations of the antigens during the course of treatment. Treatment may be continued, discontinued, or modified according to the indication that one or more treatment options (e.g., different antigens or mixtures thereof, different adjuvants, different modes of administration, etc.) may be more effective than others for the subject based on the detected immune deviation.

Immune deviation monitoring may be performed as desired. In some embodiments, a sample is collected during or prior to the start of immunotherapy, and a subsequent sample or samples are collected about 2 weeks, about 1, 2, 3, 4, 5, or 6 months, about 1 year, etc., afterwards. The frequency of allergy-specific CD4+ T cells is determined and compared with the frequency found in previously-collected samples in order to determine whether or not the subject is showing an immune deviation. In some embodiments, the frequency of a given sample is measured close to the time of collection; however, in some embodiments, samples may also be frozen for determination at a later time, if desired.

"Subjects" that may be treated and/or monitored by methods of the present invention include both human subjects for medical purposes and animal subjects for veterinary and laboratory purposes. Other suitable animal subjects are, in general, mammalian subjects such as primates, bovines, ovines, caprines, porcines, equines, felines, canines, lagomorphs, rodents (e.g., rats and mice), etc. Human subjects are the most preferred. Human subjects include fetal, neonatal, infant, juvenile, adult and geriatric subjects.

"Treating" refers to any type of treatment or prevention that imparts a benefit to a subject afflicted with or at risk of developing an immune-related disease or illness, including, but not limited to, allergies or an allergic reaction to an antigen of interest, including improvement in the condition of the subject (e.g., in one or more symptoms), delay in the onset of symptoms or slowing the progression of symptoms, etc. As used herein, "treatment" is not necessarily meant to imply cure or complete abolition of symptoms, but refers to any type of treatment that imparts a benefit to a patient, for example, a patient afflicted with or at risk for an allergy or allergic reaction.

"Treatment effective amount", "prevention effective amount", "amount effective to treat", "amount effective to prevent" or the like as used herein means an amount of the material or composition sufficient to produce a desirable effect upon a patient inflicted with an immune disorder such as an allergy. This includes improvement in the condition of the patient (e.g., in one or more symptoms), delay in the onset or progression of the disease, etc.

A "control subject" as used herein is a subject that is known to not have an immune disorder (e.g., and allergy). In some embodiments, the Th2a subset frequency of a control subject may be used to compare with a test subject to determine if the test subject has a larger Th2a frequency, which larger frequency may indicate an immune disorder as taught herein.

Some embodiments of present invention are explained in greater detail in the following non-limiting examples.

Example 1: Determination of Allergen-Specific Th2 Cell Phenotype

Microarray analysis was used to evaluate the gene expression profiles of allergen-specific CD4+ cells between allergic and non-allergic individuals. It was found that CD161 is over-expressed in allergen-specific CD4+ cells from allergic individuals as compared to non-allergic individuals.

Figure 2:
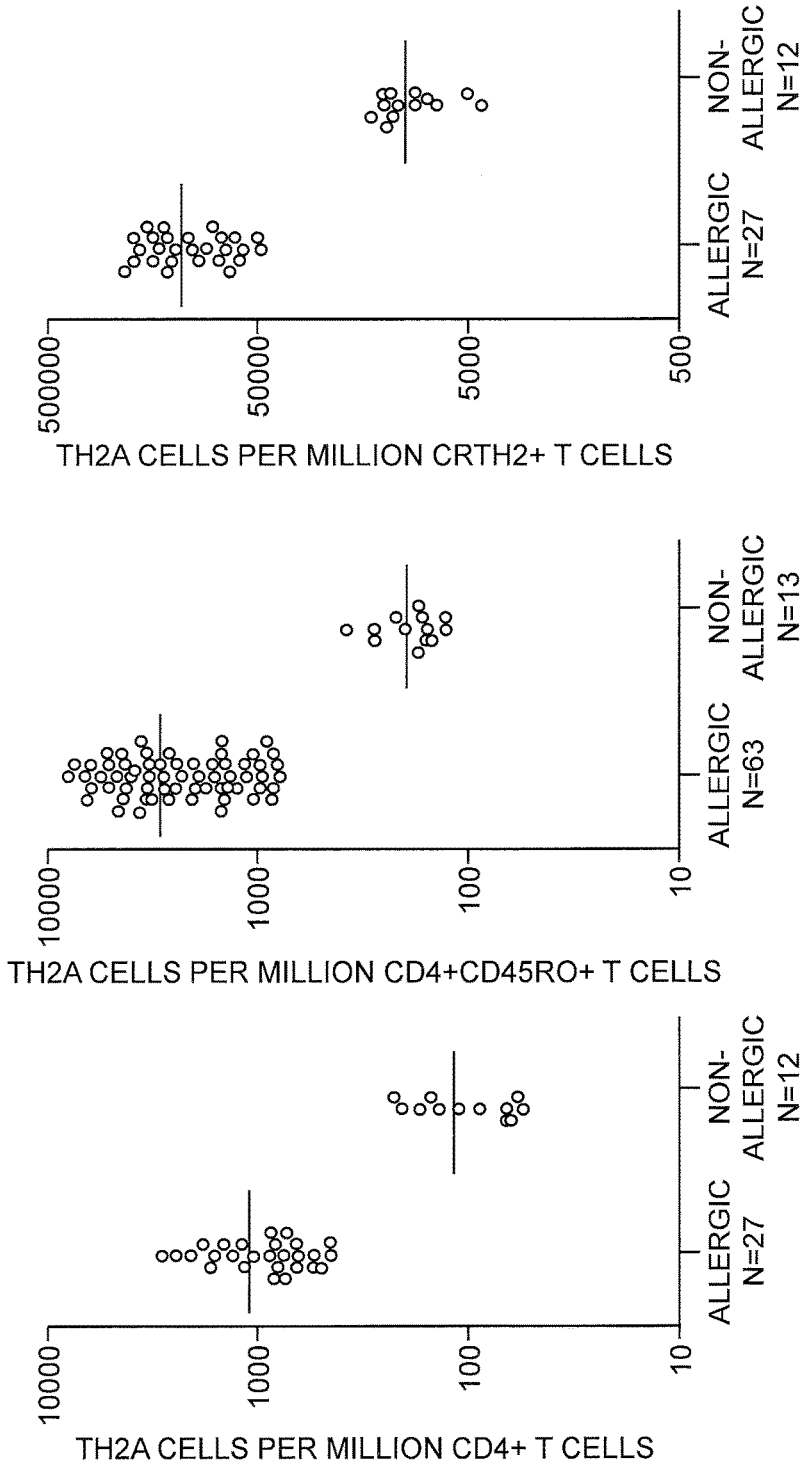
FIG. 2 shows that significant numbers of Th2a cells were exclusively observed in PBMC samples from allergic individuals.
Figure 3:
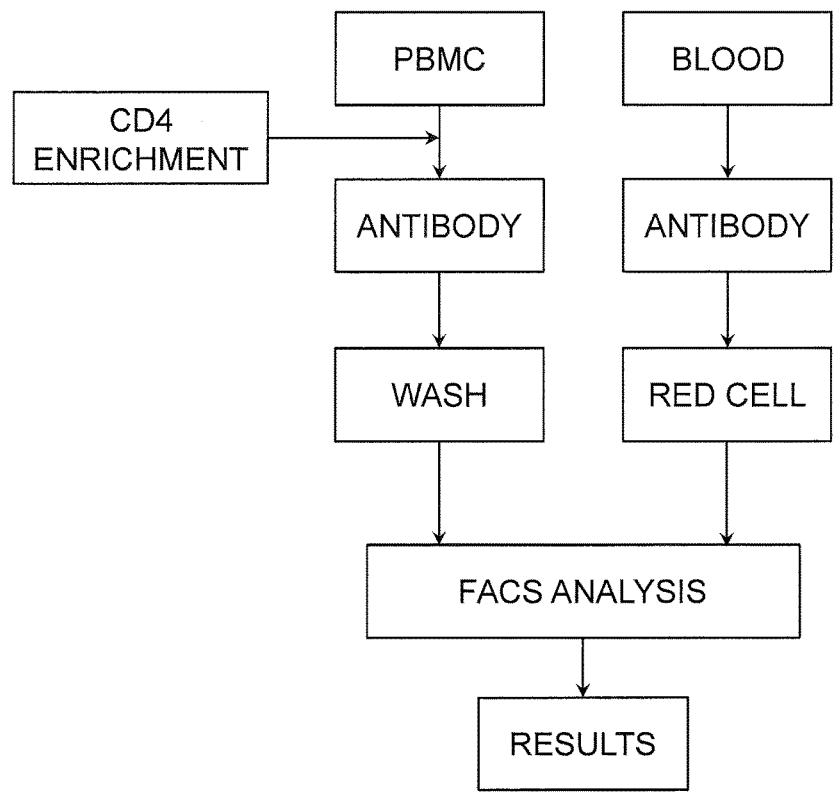
FIG. 3 provides a schematic representation of an exemplary assay that may be performed to detect Th2a cells in a biological sample.

Allergen-specific Th2 cells (Th2a) are a subset of Th2 cells having expression of CD161, CD49d and lacking CD27 and CD45RB expression. As shown in FIG. 1 and FIG. 2, significant numbers of Th2a cells were exclusively observed in allergic individuals.

Example 2: FACS Detection of CD4+ Th2a Cell Frequency

The assay is designed to identify and characterize allergen-specific CD4+ T cells by flow cytometry in either a whole blood sample or isolated PBMCs. A schematic of a representative assay is presented in FIG. 4.

For this purpose, a 4- to 6-color combination may be used. Exemplary color combinations are presented in Table 1.

CD4+ T lymphocytes are analyzed using CD4 expression. Allergen-specific CD4+ Th2 (Th2a) cells are identified as $CD4^{pos}$ $CRTH2^{pos}$ $CD27^{neg}$ $CD49d^{pos}$ $CD45RB^{neg}$ $CD161^{pos}$, whereas non-allergen-specific CD4+ Th2 cells are identified as $CD4^{pos}$ $CRTH2^{pos}$ $CD161^{neg}$.

For whole blood assay, peripheral blood samples are collected aseptically into a sterile evacuated blood collection tube with anticoagulant. Specimen should be stored at room temperature until processing (preferably less than 48 hours). The specimen should be homogenized by gentle agitation prior to pipetting.

One ml of whole blood per test is alloquated into 15 ml conical tubes and stained with antibodies cocktail for 45 minutes at room temperature, protected from light. Then 100 μl of fixative solution is added into each tube and gently vortexed for approximately 5 seconds.

Ten ml of lysing solution (room temperature) is added to each tube and vortexed vigorously, and then incubated at room temperature for 10 minutes, protected from light. The tubes are then centrifuged for 5 minutes at 200 g, and aspirate the supernatant. The lysing steps are then repeated.

The cell pellet is resuspended with 400 μl of PBS, and the cells are transferred into a (12×75 mm) FACS tube. Data is then acquired on the flow cytometer. If not analyzed within one hour, processed samples are stored between 2-8° C., protected from light, and analyzed within 6 hours.

For PBMC assay, one million freshly isolated or frozen PBMCs are alloquated into a (12×75 mm) FACS tube and stained with antibodies cocktail for 45 minutes or 20 minutes at room temperature, protected from light. Cells are washed twice with 1 ml of PBS and the cell pellet is resuspended with 400 μl or 200 μl of PBS. Data is then acquired on the flow cytometer. If not analyzed within one hour, processed samples are stored between 2-8° C., protected from light, and analyzed within 6 hours.

The flow cytometer is equipped to detect Forward Scatter, Side Scatter and a minimum of four fluorochromes are used: FITC, PE, PercP and APC.

Create Dot Plots as follows in order to detect allergen-specific CD4+ Th2 (Th2a) cells using a six- or seven-colors flow cytometer:
1. Create Dot Plot 1 as Forward Scatter vs Side Scatter.
2. Create Dot Plot 2 as CD4 vs Side Scatter or CD45RO.
3. Create Dot Plot 3 as CD4 vs CD45RB.
4. Create Dot Plot 4 as CD49d vs CD27.
5. Create Dot Plot 5 as CRTH2 vs CD161.
6. Optionally, create Dot Plot 6 as CRTH2 vs CD161.

Create regions as follows:
1. Dot Plot 1—Create an amorphous/polygonal Region A on Dot Plot 1 to include all lymphocytes and eliminate red blood cell debris, aggregates, monocyte and granulocytes.

TABLE 1

Exemplary 4- to 6-color combinations for FACS analysis of allergen-specific CD4+ T cells.

| 4-colors | 5-colors | 6-colors | 7-colors | |
|---|---|---|---|---|
| anti-CD27 + anti-CD45RB | anti-CD27 + anti-CD45RB | anti-CD27 | anti-CD27 | anti-CD27 |
| anti-CD161 | anti-CD161 | anti-CD161 | anti-CD161 | anti-CD161 |
| anti-CD4 | anti-CD4 | anti-CD4 | anti-CD4 | anti-CD4 |
| anti-CRTH2 | anti-CRTH2 | anti-CRTH2 | anti-CRTH2 | anti-CRTH2 |
| | anti-CD49d | anti-CD45RB | anti-CD45RB | anti-CD45RB |
| | | | anti-CD49d | anti-CD49d |
| | | | | anti-CD45RO |

2. Dot Plot 2—Create a rectilinear Region B on Dot Plot 2 to include all $CD4^{pos}$ and T lymphocytes (e.g., CD45RO$^{pos}$ T lymphocytes) while excluding CD4$^{neg}$ (and optionally CD45RO$^{neg}$) cells.
3. Dot Plot 3—Create a rectilinear Region C on Dot Plot 3 to include all CD4$^{pos}$CD45RB$^{neg}$ events.
4. Dot Plot 4—Create a rectilinear Region D on Dot Plot 4 to include all CD49d$^{pos}$CD27$^{neg}$ events.
5. Dot Plot 5—Create rectilinear Region E on Dot Plot 5 to include all CD161$^{pos}$CRTH2$^{pos}$ events.

Create gates as follows:
1. Dot Plot 1—Ungated to display all events.
2. Dot Plot 2—Assign "A" to Dot Plot 2 to display all lymphocytes while eliminating red blood cell debris, aggregates, monocyte and granulocytes.
3. Dot Plot 3—Assign "A" and "B" (AB) to Dot Plot 3 to display all CD4$^{pos}$ (and optionally CD45RO$^{pos}$) T lymphocytes while excluding CD4$^{neg}$ (and optionally CD45RO$^{neg}$) cells.
4. Dot Plot 4—Assign "A", "B" and "C" (ABC) to Dot Plot 4 to display all CD4$^{pos}$ (and optionally CD45RO$^{pos}$) CD45RB$^{neg}$ lymphocytes.
5. Dot Plot 5—Assign "A", "B", "C" and "D" (ABCD) to Dot Plot 5 to display all CD4$^{pos}$ (and optionally CD45RO$^{pos}$) CD45RB$^{neg}$ CD27$^{neg}$ CD49d$^{pos}$ lymphocytes.
6. Dot Plot 6—Assign "A", "B", "C", "D" and "E" (ABCDE) to Dot Plot 6 to display all CD4$^{pos}$ (and optionally CD45RO$^{pos}$) CD45RB$^{neg}$ CD27$^{neg}$ CD49d$^{pos}$ CD161$^{pos}$ CRTH2$^{pos}$ lymphocytes.

To calculate Th2a cell frequencies per total CD4+ T cells, determine the total number of CD4$^{pos}$ T cells in Dot Plot 3; then determine the total of Th2a cells in Dot Plot 6 (in gate ABCDE). Th2a cell frequency per total CD4+ T cells=(# of Th2a cells)/(# of CD4+ T cells).

To calculate Th2a cell frequencies per total memory CD4+ T cells, determine the total number of CD4$^{pos}$ CD45RO$^{pos}$ T cells in Dot Plot 3 (Gate AB); then determine the total of Th2a cells in Dot Plot 6 (in gate ABCDE). Th2a cell frequency per total memory CD4+ T cells=(# of Th2a cells)/(# of CD4+ CD45RO+ T cells).

To calculate Th2a cell frequencies per total CRTH2+ CD4+ CD45RO+ T cells, determine the total number of CRTH2$^{pos}$ T cells in CD4$^{pos}$ CD45RO$^{pos}$ T cells (Gate AB); then determine the total of Th2a cells in Dot Plot 6 (in gate ABCDE). Th2a cell frequency per total CRTH2+ CD4+ T cells=(# of Th2a cells)/(# of CD4+ CD45RO+ CRTH2+ T cells).

Example 3: Th2a Cell Frequencies are Monitored in Grass Pollen Allergic Patients Receiving Allergen-Specific Immunotherapy Th2a cell frequencies were monitored in grass pollen allergic patients receiving active or placebo tablets in a double blind placebo-controlled study conducted in an allergen exposure chamber. The Th2a cell frequencies were assessed in coded frozen/thawed PBMCs samples at baseline (V3), and after 2 (V6) and 4 (V7) months of sublingual immunotherapy (SLIT). Percentages of Th2a cells were normalized to 100 for each patient at baseline.

Figure 4:
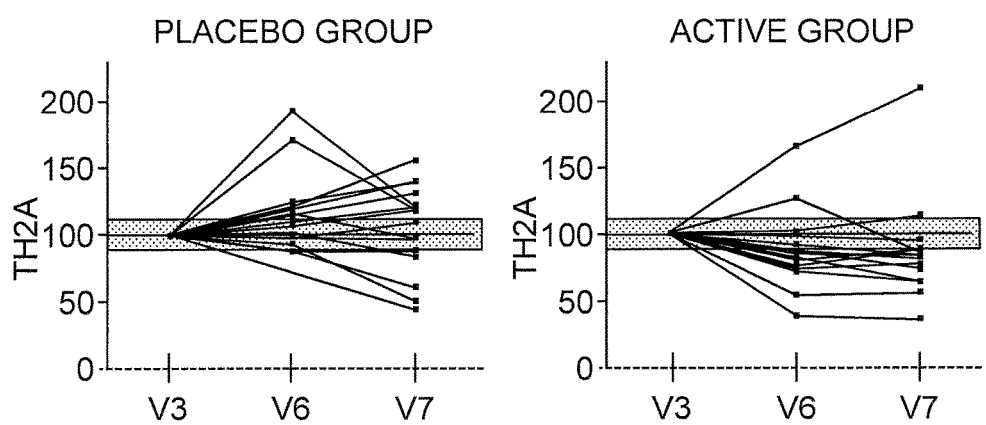
FIG. 4 demonstrates that differences in Th2a cell frequencies can be seen between patients receiving sublingual immunotherapy (SLIT) and patients receiving placebo. Th2a cell frequencies were monitored in grass pollen allergic patients receiving active or placebo tablets in a double blind placebo-controlled study conducted in an allergen exposure chamber. The Th2a cell frequencies were assessed in coded frozen/thawed PBMCs samples at baseline (V3), and after 2 (V6) and 4 (V7) months of sublingual immunotherapy (SLIT). Percentages of Th2a cells were normalized to 100 for each patient at baseline.

As shown in FIG. 4, differences are seen between the patients receiving the active tablets versus the placebo group after 2 and 4 months of treatment, demonstrating immune deviation with treatment in at least some of the patients.

The foregoing is illustrative of the present invention, and is not to be construed as limiting thereof. The invention is defined by the following claims, with equivalents of the claims to be included therein.

That which is claimed is:

1. A method of treating an allergic disorder in a mammalian subject, comprising administering an immunotherapy treatment to a subject having a significant cell frequency of CD4+ T cells that are CRTH2 positive and CD161 positive,
said method further comprising detecting a cell frequency of CD4+ T cells that are CRTH2 positive and CD161 positive in a biological sample of the subject,
wherein the detecting is carried out by a method comprising: contacting the biological sample of the subject with antibodies, said antibodies comprising anti-CD4, anti-CRTH2 and anti-CD161, and then detecting the antibodies to thereby detect the cell frequency of CD4+ T cells that are CRTH2 positive and CD161 positive in the biological sample.

2. The method of claim 1, wherein the detecting is carried out by a method comprising:
a) providing the biological sample;
b) staining the biological sample with antibodies, said antibodies comprising anti-CD4, anti-CRTH2 and anti-CD161, to thereby provide a stained sample; and
c) performing flow cytometry on the stained sample,
to thereby detect the cell frequency of CD4+ T cells that are CRTH2 positive and CD161 positive in the biological sample.

3. The method of claim 2, wherein said flow cytometry is fluorescent activated cell sorting (FACS).

4. The method of claim 3, wherein said stained sample comprises at least three fluorochromes.

5. The method of claim 3, wherein said FACS is carried out with at least a 3-color combination.

6. The method of claim 2, wherein said antibodies further comprise anti-CD49d, to detect the frequency of said CD4+ T cells that are also CD49d positive in the biological sample.

7. The method of claim 6, wherein said antibodies further comprise anti-CD45RB, to detect the frequency of said CD4+ T cells that are also CD45RB negative in the biological sample.

8. The method of claim 7, wherein said antibodies further comprise anti-CD27, to detect the frequency of said CD4+ T cells that are also CD27 negative in the sample.

9. The method of claim 2, wherein said antibodies further comprise anti-CD45RO, to detect the frequency of said CD4+ T cells that are also CD45RO positive in the sample.

10. The method of claim 1, wherein said subject is a human subject.

11. The method of claim 10, wherein said human subject is between 0 and 5 years of age, and wherein said allergic disorder is a food allergy.

12. The method of claim 1, wherein said biological sample is a human tissue sample.

13. The method of claim 1, wherein said biological sample is a whole blood sample or a peripheral blood mononuclear cell (PBMC) sample.

14. The method of claim 13, wherein said whole blood sample or PBMC sample has a volume of from 0.05 to 10 milliliters.

15. The method of claim 13, wherein said whole blood sample or PBMC sample has a volume of from 0.1 to 5 milliliters.

16. The method of claim 1, wherein said biological sample is collected from a subject afflicted with or at risk of developing an allergic disorder.

17. The method of claim 16, wherein said allergic disorder is seasonal rhinoconjunctivitis, an allergy to pet dander, a food allergy, venom anaphylaxis, or asthma.

* * * * *